US012797573B2

(12) United States Patent
Maxwell

(10) Patent No.: US 12,797,573 B2
(45) Date of Patent: Nov. 17, 2026

(54) DENTAL TOOL FOR DECREASING PAIN AT INJECTION SITE

(71) Applicant: Joshua Maxwell, Ashland, KY (US)

(72) Inventor: Joshua Maxwell, Ashland, KY (US)

(*) Notice: Subject to any disclaimer, the term of this patent is extended or adjusted under 35 U.S.C. 154(b) by 95 days.

(21) Appl. No.: 18/795,858

(22) Filed: Aug. 6, 2024

(65) Prior Publication Data

US 2026/0041873 A1 Feb. 12, 2026

(51) Int. Cl.
*A61M 19/00* (2006.01)
*A61M 5/178* (2006.01)

(52) U.S. Cl.
CPC ............ *A61M 19/00* (2013.01); *A61M 5/178* (2013.01); *A61M 2205/3606* (2013.01); *A61M 2210/0631* (2013.01)

(58) Field of Classification Search
CPC ..... A61C 19/08; A61C 19/066; A61C 19/063; A61M 19/00; A61M 5/178; A61M 2205/3606; A61M 2210/0631
USPC ........................................................... 433/90
See application file for complete search history.

(56) References Cited

U.S. PATENT DOCUMENTS 59,562 A * 11/1866 Cutter ................. A61M 15/009 128/200.14
1,798,188 A * 3/1931 Brown ................... A47K 7/028 15/244.1
2,070,097 A * 2/1937 Stipe ....................... F25C 5/043 241/266
2,070,773 A * 2/1937 Arndt ...................... F25C 5/043 62/320
2,360,250 A * 10/1944 Mallard .................. A23G 9/00 D15/90
3,194,237 A * 7/1965 Rubin .................. A61J 1/2089 D24/112
3,563,239 A * 2/1971 Hill ....................... A61M 19/00 606/21
3,948,261 A * 4/1976 Steiner ............... A61B 10/0035 215/307
4,440,167 A * 4/1984 Takehisa ................ A61B 18/02 433/32

(Continued)

FOREIGN PATENT DOCUMENTS

CN 1429631 A * 7/2003
CN 1575822 A * 2/2005 ........... A61B 17/205

(Continued)

OTHER PUBLICATIONS

Seon-Hee Han & In-Bog Lee, Effect of vibration on adaptation of dental composites in simulated tooth cavities, Korea-Australia Rheology Journal, Nov. 2018, 241-248, 30(4), Springer, Seoul, Republic of Korea.

*Primary Examiner* — Matthew M Nelson
(74) *Attorney, Agent, or Firm* — Sheri Higgins Law, PLLC; Sheri Higgins

(57) ABSTRACT

A dental tool can include a hand piece; a head for inserting and removing from an end of the hand piece, wherein the head comprises a frame comprising at least two frame arms; and a frozen liquid contained within the frame by the at least two frame arms. The frozen liquid can be placed onto a patient's tissue in the mouth to reduce or eliminate pain from an injection of anaesthesia for dental work. The hand piece can also include a mechanical motion module that imparts mechanical motion to the tissue along with cold from the frozen liquid.

20 Claims, 3 Drawing Sheets

(56) References Cited

U.S. PATENT DOCUMENTS 5,236,419 A * 8/1993 Seney ................... A61M 5/422 604/112
5,873,844 A * 2/1999 Campero ........... A61H 23/0218 433/119
6,290,683 B1 * 9/2001 Erez .......................... A61F 7/10 604/93.01
6,752,629 B2 * 6/2004 Suzuki ................... A61C 17/20 433/119
8,469,918 B2 * 6/2013 Fallek ................... A61M 5/422 600/583
9,539,171 B2 * 1/2017 Goldberg ............... A61H 7/005
9,675,766 B2 * 6/2017 Goldberg ............... A61B 90/30
10,695,508 B2 * 6/2020 Lorberbaum ......... A61M 5/422
10,967,136 B2 * 4/2021 Fox ....................... A61M 5/422
11,132,878 B2 * 9/2021 Whitaker ............... A61B 42/10
12,102,347 B2 * 10/2024 Lorberbaum .......... A61B 17/30
2003/0100936 A1 * 5/2003 Altshuler ............... A61H 99/00 607/96
2003/0171715 A1 * 9/2003 Hommann ................ A61F 7/10 604/113
2004/0138598 A1 * 7/2004 Kortuem ............. A61F 5/05875 602/22
2004/0255388 A1 * 12/2004 Lion ......................... F16L 5/14 7/113
2005/0182364 A1 * 8/2005 Burchman ............ A61M 5/422 604/500
2009/0004628 A1 * 1/2009 Knutson .......... A61B 5/150412 433/215
2009/0062737 A1 * 3/2009 Sun ....................... A61M 5/422 604/112
2009/0062783 A1 * 3/2009 Sun ........................ A61B 18/02 604/113
2010/0022965 A1 * 1/2010 Salzman ............. A61M 5/3129 604/207
2010/0179457 A1 * 7/2010 Blaine ................ A61H 23/0263 601/46
2011/0319812 A1 * 12/2011 Goldberg .............. A61M 5/422 604/22
2012/0058218 A1 * 3/2012 Blondeau ............... A23G 9/503 426/135
2012/0209363 A1 * 8/2012 Williams, III ............ A61F 7/02 607/114
2014/0074080 A1 * 3/2014 Halaka ................. A61N 5/0616 606/16
2014/0371542 A1 * 12/2014 Goldberg .............. A61M 5/422 600/249
2015/0048085 A1 * 2/2015 Brown ................... A01N 1/142 220/228
2017/0056446 A1 * 3/2017 Schmieding ........... A01N 1/146
2017/0173274 A1 * 6/2017 McCollum ............. B65D 85/00
2019/0167915 A1 * 6/2019 Gildea .................. A61M 5/422
2019/0232032 A1 * 8/2019 Hewitt ................... A45D 40/26
2019/0298488 A1 * 10/2019 Lagrange ............. A61C 15/048
2019/0358413 A1 * 11/2019 Lane ..................... A61M 5/422
2020/0060871 A1 * 2/2020 Albanese .................. A61F 7/10
2021/0069457 A1 * 3/2021 Pilby Gomez ........ A61M 19/00
2021/0113299 A1 * 4/2021 Maxwell .................. A61C 1/14
2021/0393890 A1 * 12/2021 Lynders ................ A61M 19/00
2022/0040417 A1 * 2/2022 O'Brien ............. A61H 23/0245
2022/0168134 A1 * 6/2022 Warner ..................... A61F 7/00
2023/0293342 A1 * 9/2023 Hamad ..................... A61F 7/10 607/96
2024/0238534 A1 * 7/2024 Shaw .................. A61M 5/3286
2025/0032353 A1 * 1/2025 Saxena ..................... B06B 1/02

FOREIGN PATENT DOCUMENTS

KR 20140002311 U * 4/2014 ............... A47G 1/00
NZ 553631 A * 8/2009 ............... A61F 7/10
WO WO-2005079259 A2 * 9/2005 ............ A61M 5/422
WO WO-2024166120 A1 * 8/2024 ............... A61F 7/10

* cited by examiner

DENTAL TOOL FOR DECREASING PAIN AT INJECTION SITE

TECHNICAL FIELD

A dental tool can include a handpiece and a detachable probe head. The probe head can include a probe frame having a plurality of frame arms. The frame arms can contain a frozen liquid or a pouch filled with a frozen liquid. The frozen liquid decreases the pain at an injection site.

BRIEF DESCRIPTION OF THE FIGURES

The features and advantages of certain embodiments will be more readily appreciated when considered in conjunction with the accompanying figures. The figures are not to be construed as limiting any of the preferred embodiments.

DETAILED DESCRIPTION

Figure 1:
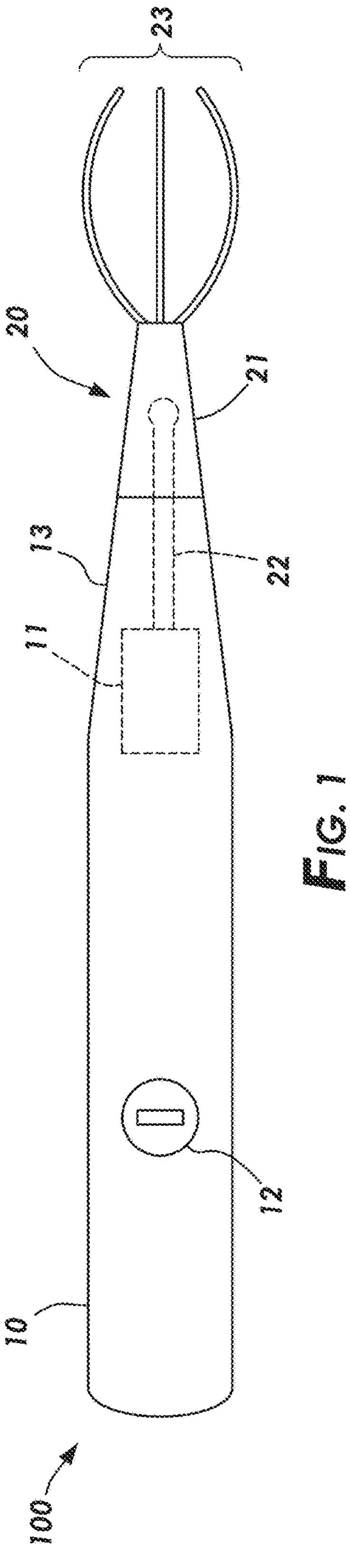
FIG. 1 is a top view of a dental tool including a hand piece and a detachable head with frame according to certain embodiments.

Dentists and endodontists perform a variety of procedures on a patient, for example filling a cavity, performing a root canal, or performing otherwise painful teeth cleanings. During these types of dental procedures, it is often necessary to inject a liquid anesthetic into an area of the patient's mouth, for example into the gums at one or more locations. The anesthetic is injected into the nerves at or near the site of the procedure such that during the procedure, the patient does not feel pain. As used herein, a "liquid" is a substance having a continuous phase that tends to flow and to conform to the outline of its container when the substance is tested at a temperature of 71 °F (22 °C) and a pressure of 1 atmosphere (atm) (0.1 megapascals (MPa)). A "gel" is a colloid containing aggregates of fine particles dispersed in a continuous liquid medium in which the liquid medium has a viscosity ranging from greater than that of water (i.e., >1 cP at 20 °C) to viscous enough to behave more or less as a solid (i.e., does not flow or conform to the outline of a container). Viscosity is a measure of the resistance of a fluid to flow, defined as the ratio of shear stress to shear rate. Viscosity can be expressed in units of (force*time)/area. For example, viscosity can be expressed in units of dyne*s/cm$^2$ (commonly referred to as Poise (P)) or expressed in units of Pascals/second (Pa/s). However, because a material that has a viscosity of 1 P is a relatively viscous material, viscosity is more commonly expressed in units of centipoise (cP), which is 1/100 P.

It can be quite painful as the needle used to inject the anesthetic is pushed into the tissue in the patient's mouth. Therefore, a dentist most often uses a topical anesthetic that is sprayed onto the injection site tissues to reduce the amount of pain during the injection. However, spray topicals do not penetrate far enough down into the injection site tissues such that the patient has no pain at all during the injection. As used herein, the term "tissue" in relation to the injection site and all grammatical variations thereof means any surface inside a mouth of a person and any singular tissue or more than one tissue of the mouth including without limitation the gums, the hard palate, the floor of the mouth, gingiva, mucosa, periodontal ligament space, lingual tissues, or any tissue between the injection entry point spanning to a necessary anatomical location for a nerve block or local infiltration of anesthetic. By way of example, the "tissue" can be the gums and hard palate or the gums and the inside of the check.

Currently dentists will typically deliver local anesthetic without any additional modalities in order to reduce pain upon injection. Up to this point there are very few instruments, preparations, and techniques available to reduce or eliminate pain upon injection. A patient will rely on topical local anesthetics to reduce pain upon injection; however, topical anesthetics provide a very miniscule extent of relief to the patient. Topical local anesthetics only numb the outermost surface of the tissues. Therefore, patients will still feel the sharp sensation of the injection needle and burning sensation of the local anesthetic due to the epinephrine in the local anesthetic bolus injected. Epinephrine is necessary to constrict blood flow at the injection site for the purpose of maintaining a high enough concentration of the local anesthetic necessary to achieve adequate localized anesthesia. With normal blood flow to the area of the injected bolus, the local anesthetic will be carried away from the area rapidly rendering the patient without relief from pain. Local anesthetics can be warmed to near body temperature prior to injection, which can help with the pain response to local anesthetic injections; however, warming the local anesthetic only provides a minimal amount of pain reduction. In addition, injecting local anesthetic slowly can reduce pain during injection as well. With any of the traditional techniques it is nearly impossible to eliminate or significantly reduce pain during local anesthetic injections.

Thus, there is a need for an improved dental instrumentation and techniques that can be used to substantially reduce or preferably eliminate the pain during injection. It has been discovered that a dental tool can include a hand piece and a removable head. The hand piece can include a mechanical motion module for imparting mechanical motion to the head. The head can house a frozen liquid that is directly applied to the patient's tissue at the injection site prior to the injection. The mechanical motion, pressure, and/or cold from the frozen liquid is sent through the patient's nerves to the brain, where the mechanical motion, pressure, and/or cold is processed. The dental tool is held in place adjacent to the injection site during the injection. Any pain response from the injection will not or is much less likely to register in the patient's brain because the brain is already processing the mechanical motion, pressure, and/or cold. Accordingly, the dental tool is a very effective way of eliminating or reducing the amount of pain felt from the injection.

It has been discovered that utilizing 3 different modalities of pressure, cold, and vibration can substantially reduce or eliminate pain during injections in the oral cavity. Applying pressure to the injection site changes the way pain signals are transmitted to the brain, providing relief during injections. Pressure stimulation of mechanoreceptors close the gate of pain receptors through presynaptic nerve inhibition, which prevents the perception of pain. Cold is another modality that can temporarily and deeply numb the area of injection prior to delivering an anesthetic bolus intraorally. Cold causes blood vessels to constrict at the injection site. This is a biophysical reaction utilized to help conserve heat and prevent excessive heat loss from the body; however, it produces a substantially decreased sensation to the area to a degree of profound numbness. Cold activates nerve receptors called thermoreceptors. These receptors transmit signals to the brain indicating a decrease in temperature. The nerve receptors become exhausted, leading to temporary numbness or loss of feeling. Application of cold also slows down nerve transmission. Slower nerve transmission leads to a lag in the transmission of sensory information, contributing to the sensation of numbness comparable to a local anesthetic. Vibration is another modality to provide temporary and profound numbness to the area applied. Vibratory analgesia is the ability of vibration to reduce pain. It is a non-invasive pain control practice that has existed for decades and has been shown to be clinically effective. Vibration near the needle entry point provides neural distraction to minimize pain by significantly reducing the nerve's ability to transmit pain while it is transmitting vibration. Nerves in the oral cavity have a difficult time transmitting vibration and pain at the same time due to the fact that the transmission of vibration creates a negative neural feedback loop that creates a blockage of pain transmission to the brain. A device that can deliver local topical anesthetic, cold, vibration and application of pressure will profoundly reduce or eliminate pain during dental injections.

According to certain embodiments, a dental tool can include a hand piece; a head for inserting into and removing from an end of the hand piece, wherein the head comprises a frame comprising at least two frame arms; and a frozen liquid contained within the frame by the at least two frame arms.

According to certain other embodiments, a method of reducing pain to an injection site of a tissue of a mouth can include inserting a dental tool into the mouth, wherein the dental tool comprises: a hand piece; a head for inserting and removing from an end of the hand piece, wherein the head comprises a frame comprising at least two frame arms; and a frozen liquid contained within the frame by the at least two frame arms; contacting the injection site of the tissue of the mouth with the frozen liquid for a period of time; and then using a syringe to inject an anesthetic into the tissue at the injection site.

It is to be understood that any discussion of any of the components disclosed herein is meant to include the dental tool and methods of using the dental tool without the need to repeat information throughout. By way of example, any discussion related to the hand piece or head is meant to apply to the dental tool and the method embodiments.

Turning to the figures, FIG. 1 shows a dental tool 100 according to certain embodiments. The dental tool 100 includes a hand piece 10. The hand piece 10 can be made from a variety of materials, for example, a rigid plastic. The hand piece 10 can have a generally cylindrical-shaped body with a curved end and an opposing end 13. The hand piece 10 can have length dimensions in the range of 5 inches (in.) to 8 in. (12.7 centimeters (cm) to 20.3 cm). The hand piece 10 can have a diameter in the range of 0.5 in. to 2.5 in. (1.25 cm to 6.4 cm). According to certain embodiments, the hand piece 10 has dimensions selected such that a user (e.g., a dentist) can comfortably grasp the hand piece 10, while at the same time not being too large to obscure the view into a patient's mouth.

Figure 3:
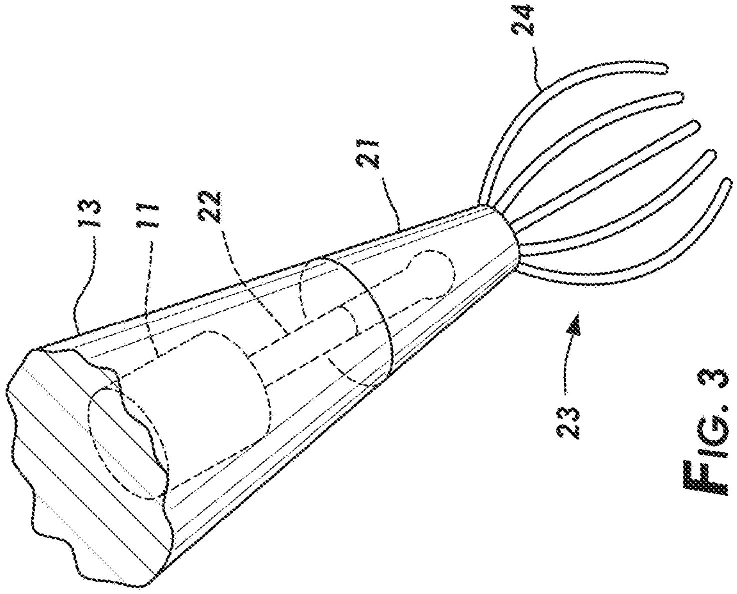
FIG. 3 is an enlarged view showing the head inserted into an end of the handpiece.
Figure 2:
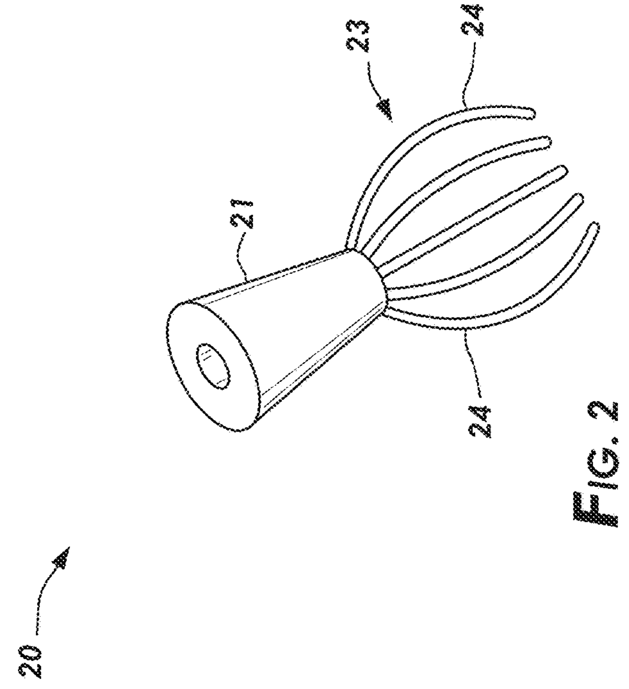
FIG. 2 is a front perspective view of the head showing a total of 5 frame arms according to certain embodiments.

The dental tool 100 also includes a head 20 for inserting into and removing from the end 13 of the hand piece 10. Accordingly, the head 20 is detachable. The head 20 can include a body 21, an opening for receiving an insertion member 22, and a frame 23. The frame 23 can include at least two frame arms 24. The frame arms 24 and the body 21 are a one-piece unit wherein the frame arms extend down and away from a first end of the body. The opening for receiving the insertion member 22 can be located at a second end of the body 21 that is opposite of the first end and can be used to removably attach and secure the head 20 to the hand piece 10, for example as shown in FIG. 3. The head 20 can be detached from the hand piece 10 by pulling the body 21 away from the end 13 of the hand piece 10. The body 21 and insertion member 22 can be made from the same type of material or different materials. The material can be selected from hard plastics, metals, metal alloys, or other rigid materials.

The dental tool 100 further includes a mechanical motion module 11. The mechanical motion module 11 can be located within the body of the hand piece 10. The hand piece 10 can further include a switch 12 for activating and deactivating the mechanical motion module 11 (i.e., an on/off switch). The switch 12 can be located on the outside of the body of the hand piece 10 such that a user can easily activate and deactivate the mechanical motion module 11. The insertion member 22 can extend from the mechanical motion module 11 and out of the end 13 of the hand piece 10. The insertion member 22 can have dimensions and a shape that matingly engages with the opening of the body 21 of the head 20. In this manner, once the head 20 is pushed onto the insertion member 22, then the head 20 is secured to the hand piece 10.

The mechanical motion module 11 imparts mechanical motion to the head 20. The mechanical motion can be rotary, oscillating, vibrating, or reciprocating. Rotary motion will impart circular rotation to the head 20—that is the body 21 and frame 23. Oscillating motion will impart repeated back and forth or circular motion to the head 20. Vibrating motion will impart random motion in a multitude of directions to the head 20. Reciprocating motion will impart a repetitive up-and-down or back-and-forth linear motion to the head 20.

A frozen liquid is contained within the frame 23 by the frame arms 24. As used herein, the term "frozen liquid" means any substance that is a liquid or has a liquid phase (as in the case of a gel) at a temperature of 71 °F (22 °C) and a pressure of 1 atmosphere but undergoes a phase change to a solid at a temperature less than or equal to the freezing point of the substance, and changes phases back to a liquid via thawing and melting when the temperature is greater than the freezing point of the substance. The substance can be without limitation, fresh, distilled, deionized, or purified water; a saline solution (i.e., water with a water-soluble salt dissolved therein); or a gel, such as a gel made from water (liquid phase) and a water-absorbent polymer or a super-absorbent polymer (SAP) that is capable of absorbing and retaining the water. A local anesthetic, such as a 20% benzocaine solution, can also be included in the substance. In this manner, the topical can be used in conjunction with the cold to eliminate or substantially decrease pain at the injection site. The water-absorbent polymer can be, for example, sodium polyacrylate or a synthetic chemically altered cellulose. By way of example, the freezing point of deionized water is 32 °F (0 °C); and the freezing point of a saline solution, which is dependent on the concentration of the water-soluble salt, can range from 31.46 to 20.19 °F (−0.3 to −6.56 °C).

The frame arms 24 can be made from a variety of materials. Preferably, the material is rigid enough to contain the frozen liquid without deforming or bending to the point that the frozen liquid is no longer contained within the frame arms 24. It is to be understood that the frame arms 24 can have some flexure or bending, for example to allow insertion of a pouch as will be discussed below, but not enough flexure or bending that the frame arms 24 break or allow some or all of the frozen liquid to fall out of the frame arms. The material for the frame arms 24 can be without limitation a metal, metal alloy, plastic, nylon, or rubber. As used herein, the term "metal alloy" means a mixture of two or more elements, wherein at least one of the elements is a metal. The other element(s) can be a non-metal or a different metal. By way of example, the metal or metal alloy for frame arms 24 include, but are not limited to, aluminum, stainless steel, or nickel titanium.

The frame arms 24 can have a variety of dimensions. The length of the frame arms 24 can range from 0.5 to 1.5 inches (12.7 to 38.1 millimeters (mm)). The frame arms 24 can be solid and have a thickness ranging from 0.1 to 0.25 inches (2.54 to 6.35 mm). The frame includes at least 2 frame arms. The frame arms can be offset from each other and form a line. As can be seen in the Figures, there can be 3 or more frame arms, including a central frame arm 24 and two or more additional frame arms 24 located around the central frame arm. The central frame arm can be straight and extend down from a central point of the body 21. The two or more additional frame arms 24 can be curved or straight and extend down from the body 21 at spaced locations outside or around the central frame arm. According to other embodiments, a central frame arm is not included, and the frame 23 includes 3 or more frame arms 24 offset from each other to form a geometric shape when viewing the frame 23 from a bottom view looking towards the body 21. This embodiment can be useful when using a pouch 40 as discussed below otherwise the central frame arm could puncture the pouch. The geometric shape can be a circle, oval, triangle, square, or rectangle. In the case where there is a central frame arm, then the additional frame arms can still create the same geometric shapes listed above wherein the central frame arm would be located in the middle or center of the geometric shape. In this manner, the frame arms 24 are offset from each other and spaced far enough apart to contain the frozen liquid. The geometric shapes can have dimensions, such as length, width, a side of the triangle, or diameter, in a range of 0.05 to 0.25 inches (1.27 to 6.35 mm). Preferably, the dimensions of the shape of the frame arms are selected such that the frame 23 with the frozen liquid can be easily inserted into a patient's mouth without obstructing the view of the injection site.

Figure 4A:
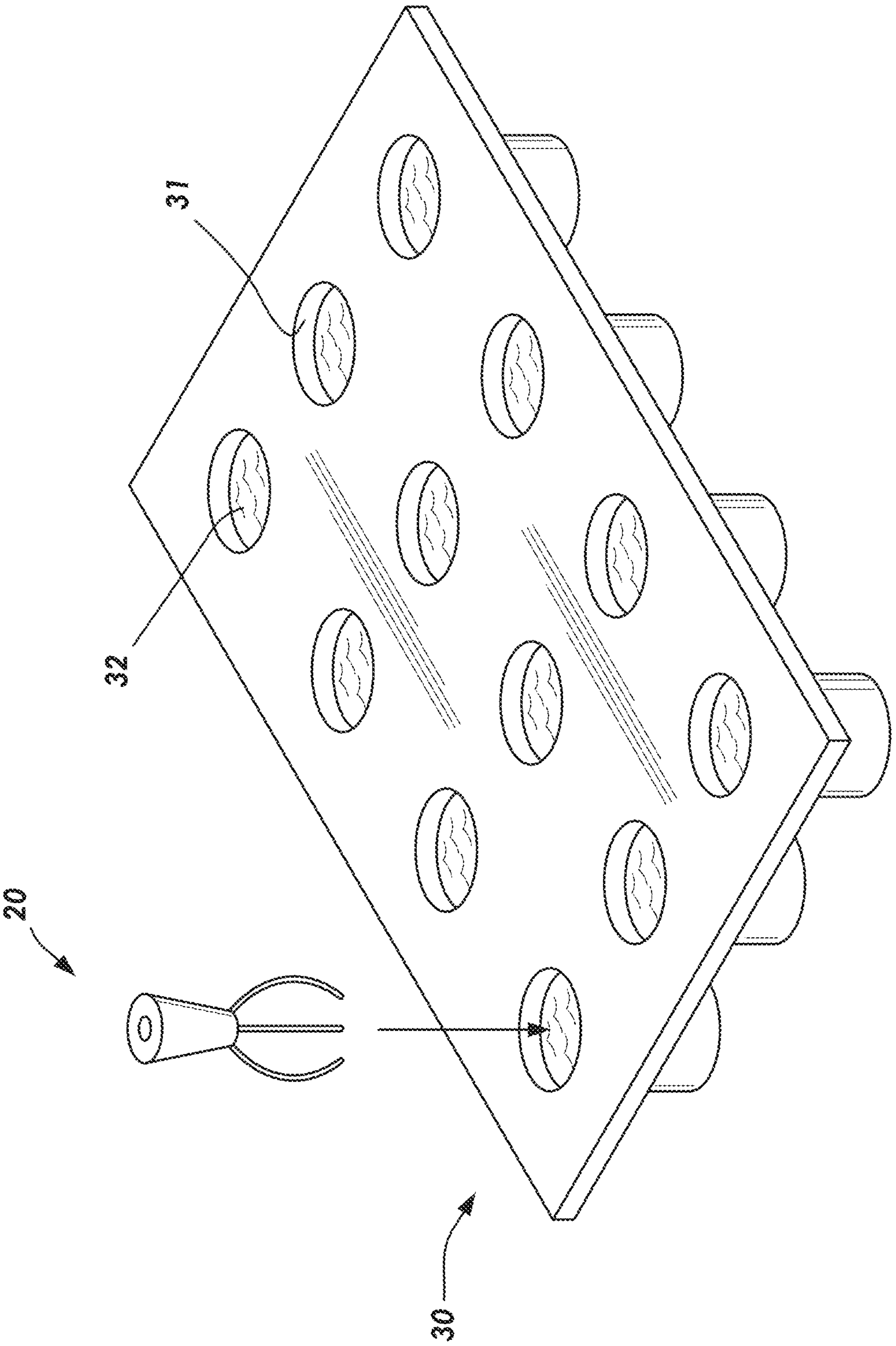
FIG. 4A is a top perspective view showing the head prior to insertion into a tray housing a liquid according to certain embodiments.
Figure 4B:
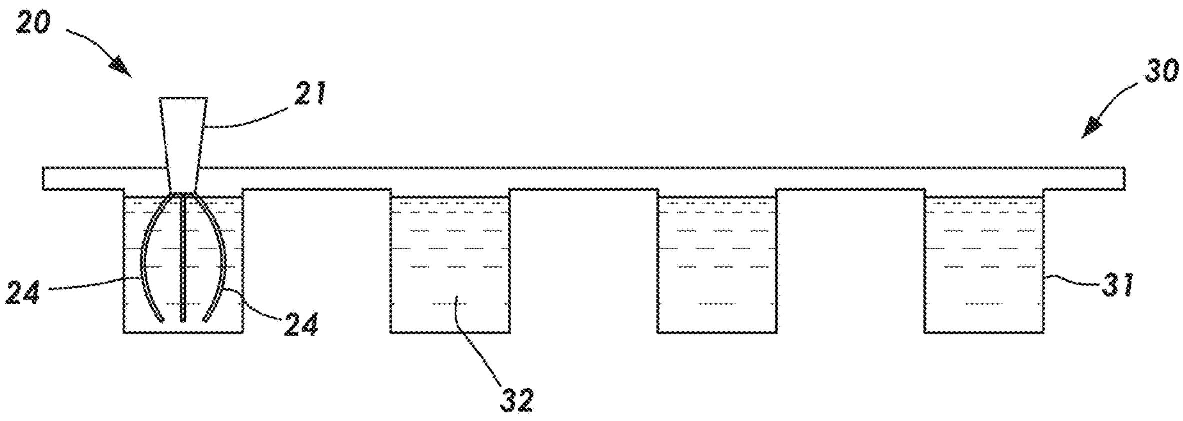
FIG. 4B is a side view of the tray of FIG. 4A after the head has been inserted into a tray cup.

Turning to FIGS. 4A and 4B, a tray 30 can include one or more tray cups 31. The tray cups 31 can be filled with the liquid 32 in liquid form that is to be frozen. According to other embodiments, each tray cup can be a standalone cup that is not included in a tray with other cups. The head 20 can be held by the body 21, for example, and the frame arms 24 can be lowered into the liquid 32. The tray cups 31 can have dimensions such that all of the frame arms 24 (e.g., 2, 3, 4, 5, etc. frame arms) can be placed into the tray cups 31. By way of example, the circumference or perimeter of the tray cups 31 can be larger than the circumference or perimeter of the frame arms 24. The depth of the tray cups 31 can be less than, greater than, or equal to the length of the frame arms 24. In this manner, the top of the frame arms 24 at the connection point to the body 21 can be located above a top edge of the tray 30 when viewing the tray from the side as shown in FIG. 4B, below the top edge of the tray, or flush with the top edge of the tray. The amount of liquid 32 that is poured into the tray cups 31 can be less than or equal to the amount that is needed to completely fill the tray cups 31. Accordingly, the liquid 32 may or may not come up the entire length of the frame arms 24 as measured from a bottom end to an opposing top end that is connected to the body 21 of the head 20. Preferably, a sufficient length of the frame arms 24 is submerged within the liquid 32 such that a desired volume of frozen liquid is contained within the frame arms 24 for each of the heads 20. The desired volume of frozen liquid can be selected based in part on the melting rate of the particular liquid used and the total length of time the frozen liquid will need to be placed against the tissue in the patient's mouth. By way of example, a single ice cube of pure water can completely melt at a temperature of 75 °F in about 90 minutes. However, the temperature in a patient's mouth is generally closer to 93 °F, so if the liquid needs to remain frozen for at least 30 minutes, then a larger volume of the frozen liquid may need to be used compared to the liquid needing to remain frozen for only 15 minutes. According to certain embodiments, the head 20 is inserted into the liquid 32 in the tray cups 31 such that the tips or ends of the frame arms do not reach all the way to the bottom of the tray cups. Accordingly, some of the frozen liquid can extend down from the tips or ends of the frame arms. It is to be understood, that some of the frozen liquid will begin to melt after removal from a freezer, however a sufficient volume of the liquid should remain frozen for the desired amount of time to be held on the patient's tissue. In this manner during use, as the frozen liquid starts to melt—especially if the melting is faster at the tips or ends of the frame arms that the frozen liquid is in contact with the patient's tissues—the tips or ends of the frame arms will not poke or make contact with the patient's tissues. According to these embodiments where the tray is used, the frame 23 and frame arms 24 can be made from a material that is inflexible.

The methods can include placing a volume of the liquid 32 into the tray cups 31 and inserting the frame arms 24 into the liquid 32 in the cups. The methods can further include placing the tray 30 and the heads 20 into a freezer until the liquid 32 has completely frozen. The freezer needs to be at a temperature less than or equal to the freezing point of the liquid to ensure that the liquid completely freezes. A stabilizer can be used to ensure that the head 20 does not fall over and thus, ensure that the frame arms remain in the tray cups and the liquid. Alternatively, the dimensions of the tray cups 31 and the frame arms 24 can be selected such that the tray cups are just slightly larger than the dimensions of the frame arms. In this manner, once inserted into the tray cups, the head will be secured from falling over and the frame arms will remain submerged in the liquid.

The methods can also include removing the heads 20 with the frozen liquid from the tray cups 31 after the liquid has completely frozen. If the tray 30 is made from a solid material such as a metal or metal alloy, then the head and frozen liquid may not be easily removed as soon as the tray is taken out of the freezer. If this is the case, then the tray can be placed at room temperature for a few minutes until the frozen liquid residing at the interface of the tray cups begins to thaw some, which allows the heads and the frozen liquid to be removed from the tray. Alternatively, a person can wrap their hands around the outside of the tray cups to slightly thaw the frozen liquid and then remove the heads with the frozen liquid. The tray 30 can also be made of a flexible silicone material, which can be helpful in unmolding the frozen liquid and heads from the cups. The tray 30 can remain in the freezer until each head 20 is ready for use. When needed for a patient, the head with the frozen liquid can then be individually removed from its tray cup for use and the tray placed back in the freezer. Alternatively, all of the heads with the frozen liquid can be removed from their tray cups and placed back into a freezer without the tray so the liquid remains frozen until ready for use. This alternate embodiment may be useful so each of the heads with the frozen liquid contained within the frame arms can be wrapped with a plastic or other material to decrease the amount of evaporation that takes place while residing in the freezer.

Figure 5A:
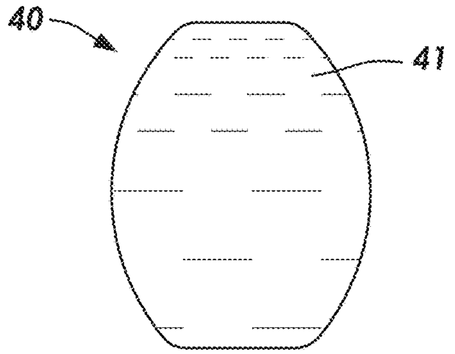
FIG. 5A is an enlarged view of a pouch housing a liquid according to certain embodiments.
Figure 5B:
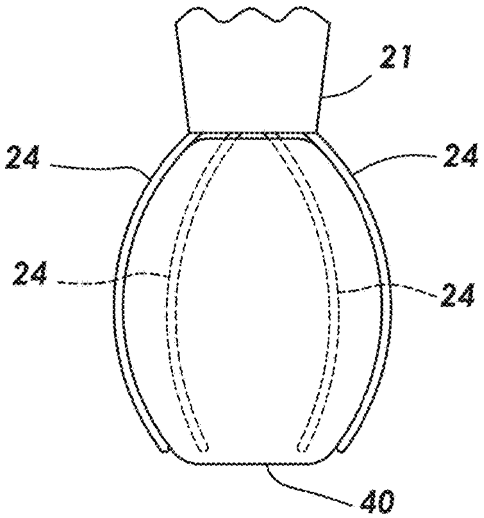
FIG. 5B is an enlarged view showing the pouch of FIG. 5A inserted into the frame arms of the head.

FIGS. 5A and 5B show a different embodiment for the frame arms 24 containing the frozen liquid. FIG. 5A shows a pouch 40 with the liquid 41 located within the pouch. The pouch 40 can have dimensions such that it fits inside the frame arms 24 as shown in FIG. 5B. The pouch 40 can be made of a durable, flexible, leakproof material, such as plastic or rubber. The pouch 40 can have an opening (not shown) for filling the pouch with the liquid 32 that is to be frozen. The opening can have a closure so the liquid 41 does not flow out of the pouch 40 after filling. After filling the pouch 40 with the liquid 41 to be frozen, the pouch 40 can be placed inside the frame arms 24 and the head 20 can then be placed in a freezer to freeze the liquid within the pouch. Alternatively, after the pouch 40 is filled with the liquid 41, the pouch 40 can be placed in a freezer until the liquid 41 is completely frozen. Then when it is time to use the frozen liquid on a patient, the pouch 40 with the frozen liquid can be removed from the freezer and inserted into the inside of the frame arms 24 for use. According to this embodiment, the frame arms 24 can be made from a material that is slightly flexible to be useful in placing the pouch with the frozen liquid inside the frame arms as the frozen liquid is a solid and may not allow the pouch to be flexible enough for insertion. However, the frame arms should not be so flexible that there is a risk of the arm breaking during insertion of the pouch with the frozen liquid inside. As shown in FIG. 5B, a bottom of the pouch 40 can extend below the tips or ends of the frame arms 24 such that the tips or ends do not make contact with a patient's tissues and instead just the bottom of the pouch with the frozen liquid is in contact with the tissues. After use on a patient, the pouch 40 can be removed from the frame arms 24 and either drained of the liquid after it has completely melted or left within the pouch, and the pouch can be thoroughly cleaned and sanitized for re-use, or the pouch can be thrown away and not re-used.

In use, the head 20 can be removably attached to the hand piece 10 by inserting the body 21 onto the insertion member 22. The frozen liquid can then be placed in the patient's mouth such that the frozen liquid contacts the tissue of the mouth at the injection site. The user (e.g., a dentist) can hold the dental tool 100 such that the tissue is contacted with the frozen liquid for a period of time. The period of time can be a time sufficient to numb the tissues prior to injection, for example. The period of time can be in a range of 1 minute to 5 minutes. The user can also spray a topical anesthetic onto the tissue around the injection site prior to contacting the tissue with the frozen liquid. The user can then move the frame arms 24 that contain the frozen liquid away from the injection site, while still keeping the frozen liquid in contact with tissue of the patient's mouth near the injection site, and then use a syringe to inject an anesthetic into the tissue at the injection site. The switch 12 of the mechanical motion module 11 can be turned on such that mechanical motion is imparted onto the tissue of the patient while concurrently having the frozen liquid in contact with the tissue while the user is injecting the anesthesia into the tissue using the syringe. The frozen liquid and the mechanical motion that is applied to the tissue at the injection site or adjacent to the injection site during the injection causes a feedback mechanism of pain-transmitting nerves, thereby neutralizing the ability of these nerves to transmit the pain response while the needle of the syringe is inserted into the tissue and during the injection of the anesthesia. While the nerves are transmitting the benign physical response to the cold from the frozen liquid and optionally the mechanical motion, there is a natural physiological response to block all other uncomfortable responses through the neural negative feedback mechanism; thereby, greatly reducing or eliminating the pain that is registered during the injection of the anesthesia. In the case where there is more than one injection site or more than one injection needed at a different time interval, then the process can be repeated for each injection site or each injection. In some cases, the same frozen liquid can be used because it has not thawed enough such that it cannot be used. In other cases, too much thawing has occurred to be used and a new head with frozen liquid would need to be used.

After the anesthesia has been injected into the tissue, the syringe and the dental tool 100 can be removed from the patient's mouth. If using the mechanical motion module 11, then the switch 12 can be turned to the off position on the hand piece 10. The head 20 can be removed from the hand piece 10. The head 20 can either be safely discarded, or the head can be thoroughly cleaned and sanitized and re-used. Accordingly, the head 20 can be disposable or re-used.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention.

As used herein, the words "comprise," "have," "include," and all grammatical variations thereof are each intended to have an open, non-limiting meaning that does not exclude additional elements or steps. While compositions, systems, and methods are described in terms of "comprising," "containing," or "including" various components or steps, the compositions, systems, and methods also can "consist essentially of" or "consist of" the various components and steps. It should also be understood that, as used herein, "first," "second," and "third," are assigned arbitrarily and are merely intended to differentiate between two or more frame arms, heads, etc., as the case may be, and does not indicate any sequence. Furthermore, it is to be understood that the mere use of the word "first" does not require that there be any "second," and the mere use of the word "second" does not require that there be any "third," etc.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A dental tool comprising:
- a hand piece, wherein the hand piece comprises an insertion member or an opening located at a first end of the hand piece;
- a head for inserting onto and removing from the first end of the hand piece, wherein the head comprises;
  - a body, wherein the body comprises a first end and a second end, wherein the first end and the second end are opposite from each other, wherein the second end is located adjacent to the first end of the hand piece; and
  - a frame comprising at least two frame arms, wherein the frame arms individually extend down and away from the body at the location of the first end of the body in a direction opposite from the second end of the body and opposite from the first end of the hand piece; and
- a frozen liquid contained within the frame by the frame arms.

2. The dental tool according to claim 1, wherein the hand piece comprises the insertion member, and wherein an opening for receiving the insertion member is located on the second end of the body.

3. The dental tool according to claim 2, wherein the insertion member is inserted into the opening of the body of the head to secure the head to the hand piece.

4. The dental tool according to claim 1, wherein the frozen liquid is a substance selected from the group consisting of fresh, distilled, deionized, or purified water; a saline solution; a gel; and combinations thereof.

5. The dental tool according to claim 4, wherein the frozen liquid is a gel that comprises water as a liquid phase and a water-absorbent polymer or a super-absorbent polymer that absorbs and retains the water.

6. The dental tool according to claim 1, wherein the frame is made from a material selected from a metal, a metal alloy, plastic, nylon, or rubber.

7. The dental tool according to claim 1, wherein the frame arms have a length in a range from 0.5 to 1.5 inches.

8. The dental tool according to claim 1, wherein the frame arms are offset from each other and form a line or a geometric shape.

9. The dental tool according to claim 8, wherein the geometric shape is a circle, oval, triangle, square, or rectangle.

10. The dental tool according to claim 9, wherein the frame comprises at least 3 frame arms that form the geometric shape and further comprising a central frame arm located in or near the center of the geometric shape.

11. The dental tool according to claim 1, further comprising a pouch, and wherein the pouch contains the frozen liquid, and wherein the pouch is positioned within an inside of the frame arms.

12. The dental tool according to claim 1, wherein the head is disposable or re-useable.

13. The dental tool according to claim 1, further comprising a mechanical motion module that imparts mechanical motion to the head, wherein the mechanical motion module is located within a body of the hand piece and the insertion member extends out of an end of the hand piece, and wherein the mechanical motion is rotary, oscillating, vibrating, or reciprocating.

14. A method of reducing pain to an injection site of a tissue of a mouth comprising:
- inserting a dental tool into the mouth, wherein the dental tool comprises:
  - a hand piece, wherein the hand piece comprises an insertion member or an opening located at a first end of the hand piece;
  - a head for inserting onto and removing from the first end of the hand piece, wherein the head comprises:
  - a body, wherein the body comprises a first end and a second end, wherein the first end and the second end are opposite from each other, wherein the second end is located adjacent to the first end of the hand piece; and
  - a frame comprising at least two frame arms, wherein the frame arms individually extend down and away from the body at the location of the first end of the body in a direction opposite from the second end of the body and opposite from the first end of the hand piece; and
  - a frozen liquid contained within the frame by the at least two frame arms;
- contacting the injection site of the tissue of the mouth with the frozen liquid for a period of time; and then
- using a syringe to inject an anesthetic into the tissue at the injection site.

15. The method according to claim 14, wherein the period of time is a time sufficient to numb the tissue prior to injection.

16. The method according to claim 14, further comprising placing a volume of the liquid in liquid form into a tray cup and inserting the head into the tray cup such that the frame arms are wholly or partially submerged in the liquid in the tray cup, and then placing the tray cup and the head into a freezer until the liquid is completely frozen.

17. The method according to claim 16, wherein the pouch is inserted into the inside of the frame arms prior to the liquid becoming frozen.

18. The method according to claim 14, wherein a pouch contains the frozen liquid and wherein the pouch is inserted into an inside of the frame arms.

19. The method according to claim 14, wherein the frozen liquid remains in contact with the tissue of the mouth adjacent to the injection site while the anesthetic is being injected into the tissue at the injection site.

20. The method according to claim 19, wherein the dental tool further comprises a mechanical motion module that imparts mechanical motion to the head, and wherein the mechanical motion is imparted to the tissue while the anesthetic is being injected into the tissue at the injection site.

* * * * *